US012751834B2

(12) United States Patent
Becker et al.

(10) Patent No.: US 12,751,834 B2
(45) Date of Patent: Oct. 6, 2026

(54) TRANSFORAMINAL LUMBAR INTERBODY FUSION IMPLANT

(71) Applicants: Gert Stephanus Becker, Waverley (ZA); Jacob Adriaan Eksteen, Paarl (ZA); Shawn Venter, Paarl (ZA)

(72) Inventors: Gert Stephanus Becker, Waverley (ZA); Jacob Adriaan Eksteen, Paarl (ZA); Shawn Venter, Paarl (ZA)

(*) Notice: Subject to any disclaimer, the term of this patent is extended or adjusted under 35 U.S.C. 154(b) by 0 days.

(21) Appl. No.: 18/998,711

(22) PCT Filed: May 28, 2024

(86) PCT No.: PCT/IB2024/055158

§ 371 (c)(1),
(2) Date: Jan. 27, 2025

(87) PCT Pub. No.: WO2024/246739

PCT Pub. Date: Dec. 5, 2024

(65) Prior Publication Data

US 2026/0076806 A1 Mar. 19, 2026

(30) Foreign Application Priority Data

May 29, 2023 (ZA) ................................ 2023/05711

(51) Int. Cl.

| | |
|---|---|
| ***A61F 2/44*** | (2006.01) |
| ***A61F 2/46*** | (2006.01) |
| *A61F 2/30* | (2006.01) |

(52) U.S. Cl.

CPC .......... *A61F 2/4455* (2013.01); *A61F 2/4611* (2013.01); *A61F 2002/30433* (2013.01); (Continued)

(58) Field of Classification Search

CPC ............................ A61F 2/4611; A61F 2/4455
See application file for complete search history.

(56) References Cited

U.S. PATENT DOCUMENTS

| | | | | |
|---|---|---|---|---|
| 9,579,213 B2 * | 2/2017 | Bal | ......................... | A61F 2/442 |
| 10,561,502 B2 | 2/2020 | Bernard et al. | | |

(Continued)

FOREIGN PATENT DOCUMENTS

| | | | |
|---|---|---|---|
| DE | 103 07 758 B4 | 2/2005 | |
| EP | 2 768 435 B1 | 4/2019 | |
| WO | WO-2024246739 A1 * | 12/2024 | ............ A61F 2/4611 |

OTHER PUBLICATIONS

Lee, D.C., Kim, J.Y., Kim, T.H et al. Unilateral approach with two-cage insertion for full endoscopic transforaminal lumbar interbody fusion: technical report. Acta Neurochir 164, 1521-1527 (2022). https://doi.org/10.1007/s00701-022-05168-z (Year: 2022).*

(Continued)

*Primary Examiner* — Jacqueline T Johanas
(74) *Attorney, Agent, or Firm* — Mueting Raasch Group

(57) ABSTRACT

A transforaminal lumbar interbody fusion device 10 comprises an elongate implant body 12 having opposed first and second ends 14, 16. The implant body 12 has a longitudinal axis 17. The body 12 defines a slot 18 between the first and second ends 14, 16. The slot 18 divides the implant body 12 into a first body part 20 having a first surface 22 and a second body part 24 having a second surface 26. The first surface 22 faces in a first direction A and the second surface 26 faces in an opposite direction B. The body parts 20, 24 are biased towards a configuration wherein the surfaces 22, 26 are closer to one another. The slot 18 is configured to receive an actuator for urging the body parts 20, 24 to a configuration wherein the surfaces 22, 26 are further away from each other. The device 10 comprises first and second pivot formations 30, 32 on an axis 34 transverse to the longitudinal axis 17 and on the first and second surfaces 22, 26 respectively.

18 Claims, 8 Drawing Sheets

(52) U.S. Cl.
CPC ............... *A61F 2002/30471* (2013.01); *A61F 2002/3054* (2013.01); *A61F 2002/30579* (2013.01)

(56) References Cited

U.S. PATENT DOCUMENTS

| | | | | |
|---|---|---|---|---|
| 11,376,134 | B1 * | 7/2022 | Dewey | A61F 2/4455 |
| 11,730,606 | B2 * | 8/2023 | Yoon | A61F 2/447 623/17.16 |
| 12,329,652 | B2 * | 6/2025 | Shoshtaev | A61F 2/4611 |
| 2005/0038511 | A1 * | 2/2005 | Martz | A61B 17/1606 623/17.11 |
| 2005/0113916 | A1 * | 5/2005 | Branch | A61F 2/447 623/17.11 |
| 2007/0282441 | A1 | 12/2007 | Stream | |
| 2008/0125865 | A1 * | 5/2008 | Abdelgany | A61F 2/4611 623/17.11 |
| 2011/0004314 | A1 * | 1/2011 | Baynham | A61F 2/4611 623/17.17 |
| 2011/0112642 | A1 * | 5/2011 | Tohmeh | A61F 2/46 623/17.11 |
| 2012/0101530 | A1 * | 4/2012 | Robling | A61F 2/4455 606/279 |
| 2012/0191193 | A1 * | 7/2012 | Trieu | A61F 2/4611 623/17.16 |
| 2014/0012383 | A1 * | 1/2014 | Triplett | A61F 2/4465 623/17.16 |
| 2014/0058515 | A1 * | 2/2014 | Hawkins | A61F 2/4644 623/17.16 |
| 2014/0156007 | A1 * | 6/2014 | Pabst | A61F 2/442 623/17.16 |
| 2016/0022438 | A1 * | 1/2016 | Lamborne | A61F 2/447 623/17.16 |
| 2016/0045333 | A1 * | 2/2016 | Baynham | A61F 2/446 623/17.16 |
| 2017/0231778 | A1 * | 8/2017 | Overes | A61F 2/4425 623/17.16 |
| 2017/0367843 | A1 * | 12/2017 | Eisen | A61F 2/447 |
| 2018/0116815 | A1 * | 5/2018 | Kuyler | A61F 2/447 |
| 2019/0358053 | A1 * | 11/2019 | Burkinshaw | A61F 2/4455 |
| 2021/0186709 | A1 * | 6/2021 | Weiman | A61F 2/4611 |
| 2022/0192840 | A1 * | 6/2022 | Barreiro | A61F 2/4611 |
| 2022/0241089 | A1 * | 8/2022 | Clauss | A61F 2/4455 |
| 2023/0346569 | A1 | 11/2023 | Yoon | |
| 2025/0325380 | A1 * | 10/2025 | Spann | A61F 2/447 |

OTHER PUBLICATIONS

International Search Report and Written Opinion for PCT/IB2024/055158 issued by the European Patent Office on Sep. 30, 2024; 14 pgs.

* cited by examiner

TRANSFORAMINAL LUMBAR INTERBODY FUSION IMPLANT

This application is the § 371 U.S. National Stage of International Application No. PCT/IB2024/055158, filed 28 May 2024, which claims the priority to ZA Application No. 2023/05711, filed 29 May 2023.

FIELD OF THE INVENTION

The invention relates to a surgical implant and more particularly to a transforaminal lumbar interbody fusion implant device, a kit and a method of implanting transforaminal lumbar interbody fusion implant devices.

BACKGROUND TO THE INVENTION

Transforaminal lumbar interbody fusion (TLIF) implant devices are known in the art. When a patient requires spinal surgery because of damage to an intervertebral disc located in a lumbar and/or sacral region of the patient's spine, it is sometimes necessary to use two expandable TLIF implant devices during such a surgery. The two TLIF implant devices act as spacers between two adjacent vertebrae and as such fulfil an important role in inhibiting displacement of the two vertebrae relative to each other. This allows for bone growth to occur between the two vertebrae and eventually for the two vertebrae to fuse.

The above surgery is typically performed as follows. A surgeon makes at least two incisions through skin and soft tissue of the patient's back, to expose a posterior portion of at least one vertebra located next to the damaged intervertebral disc. Then, the surgeon creates two (a first and a second) passages through posterior elements of the vertebrae adjacent to the intervertebral disc of interest, to access the intervertebral disc. The first passage may be created from the left of the adjacent vertebrae and the second passage may be created from the right of the adjacent vertebrae. The two passages are created by removing soft tissue and bone tissue from facet joints and lamina of the adjacent vertebrae to create access to the intervertebral disc and space. Once the passages are created, the surgeon removes the damaged intervertebral disc and prepares a first TLIF implant device to be implanted. The first TLIF implant device is removably attached to specialised instrumentation, which the surgeon uses to insert the first TLIF implant device through the first passage. Once the first TLIF implant device is positioned correctly between the two vertebrae, the instrumentation is used to expand the first TLIF implant device to a desired degree. The instrumentation is then detached from the first TLIF implant device and removed from the patient. In similar fashion a second TLIF implant device is implanted through the second passage.

A disadvantage of the above discussed TLIF implant devices is that two passages are required to position the two TLIF implant devices between the patient's vertebrae. This results in unnecessarily long surgery times and unnecessary tissue damage which in turn may lead to undesirable effects, such as longer patient recovery times and more pain experienced by the patient.

OBJECT OF THE INVENTION

It is an object of the present invention to provide a transforaminal lumbar interbody fusion (TLIF) implant device, a kit and a method of implanting a TLIF implant device with which the applicant believes that above-discussed disadvantages may at least be partially overcome, or which would provide a useful alternative to known TLIF implant devices and methods of implanting TLIF devices.

SUMMARY OF THE INVENTION

According to a first aspect of the invention, there is provided a transforaminal lumbar interbody fusion implant device comprising:

- an elongate implant body having opposed first and second ends, the implant body having a longitudinal axis and the implant body defining a slot between the first end and second end dividing the implant body into:
  - a first body part having a first surface which in use, and when the body is located in an intervertebral space, faces in a first direction towards a first vertebra; and
  - a second body part having a second surface which in use, and when the body is located in the intervertebral space, faces in an opposite direction and towards a second vertebra which is adjacent to the first vertebra,
- the first and second body parts being biased towards a first configuration wherein the first and second surfaces are relatively closer to each other, the slot being configured to receive an actuator for urging the first and second body parts to a second configuration wherein the first and second surfaces are relatively further away from each other; and
- first and second pivot formations on an axis transverse to the longitudinal axis of the implant body and on the first and second surfaces respectively for enabling pivotal movement of the implant body about the transverse axis.

The transverse axis may be perpendicular to the longitudinal axis.

The implant body may be of unitary construction.

The implant body may be manufactured of a resiliently deformable material.

The device may comprise an actuator which is selectively manipulatable to urge the first and second body parts to the second configuration.

The slot may extend from the first end towards the second end.

The implant body comprises at least one link between the first body part and the second body part.

The at least one link may be integrally formed with the body.

The at least one link may be resiliently deformable.

The implant body may define an opening at the second end for receiving the actuator.

The actuator may comprise a bolt having an external thread and the implant body may comprise an internal thread located adjacent the opening for cooperating with the external thread.

The first and second pivot formations may be located towards the first end.

The first and second pivot formations may comprise at least one of: pins and circular formations.

The implant body may have first and second opposed sides, each side located between the first and second ends and between the first and second surfaces, and the first and second surfaces may be sloped from the first side having a first height $h_1$ towards the second side having a second height $h_2$ which is more than the first height.

The first and second body parts may be tapered from the second side towards the first side such that an angle $\alpha$ is formed between the first surface and the second surface.

The angle α may range from 1° to 20°.

Preferably, the angle α may range from 5° to 15°.

More preferably, the angle α may be 11°.

According to another aspect of the invention there is provided for a kit comprising:

- at least one transforaminal lumbar interbody fusion implant device; and
- a tool for inserting the at least one device between adjacent vertebrae and for manipulating the actuator.

According to yet another aspect of the invention there is provided for a method of implanting a transforaminal lumbar interbody fusion implant device, the device comprising a) an elongate implant body having a longitudinal axis, the body comprising a first body part and a second body part; b) first and second pivot formations located on the first and second body parts respectively, and on an axis transverse to the elongate axis of the implant body; and c) an actuator for urging the first and second body parts away from each other, the method comprising:

- creating a first posterior passage extending from a position on a first side of a midline of a vertebra to an intervertebral space;
- inserting the transforaminal lumbar interbody fusion implant device through the first passage;
- locating the transforaminal lumbar interbody fusion implant device in an initial position in the intervertebral space with the first and second pivot formations on an opposed side of the midline;
- manipulating the actuator to urge the first and second body parts away from each other; and
- pivoting the transforaminal lumbar interbody fusion implant device about the transverse axis to a final position.

Further, the method may comprise:

- inserting a second transforaminal lumbar interbody fusion implant device through the first passage; and
- locating the second transforaminal lumbar interbody fusion implant device in a position in the intervertebral space on the first side of the midline.

BRIEF DESCRIPTION OF THE ACCOMPANYING DIAGRAMS

The invention will now further be described, by way of example only, with reference to the accompanying diagrams wherein.

DETAILED DESCRIPTION OF THE INVENTION

Figure 1:
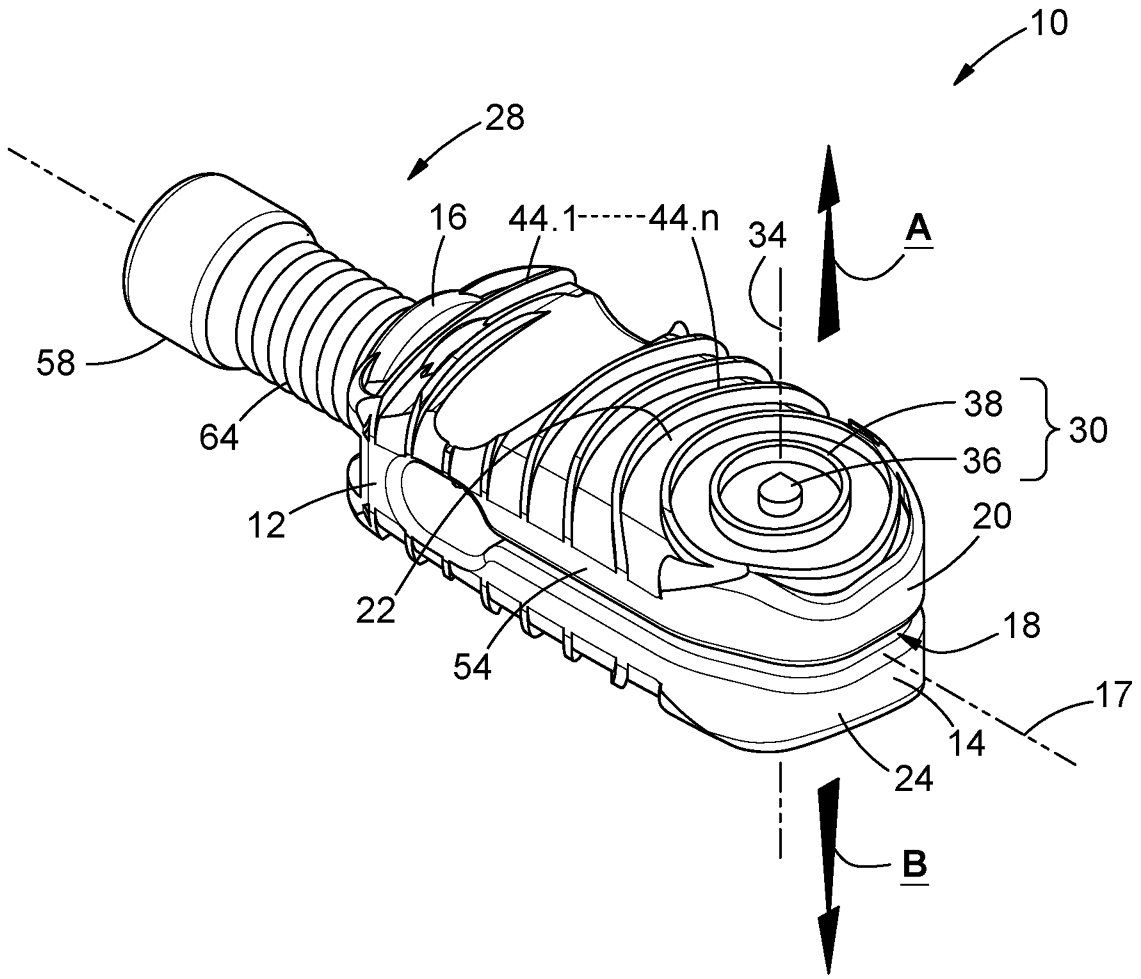
FIG. 1 is a frontal perspective view of an example embodiment of a transforaminal lumbar interbody fusion (TLIF) implant device according to the invention.

An example embodiment of a transforaminal lumbar interbody fusion (TLIF) device is generally designated by the reference numeral 10 in FIGS. 1 to 11.

Figure 2:
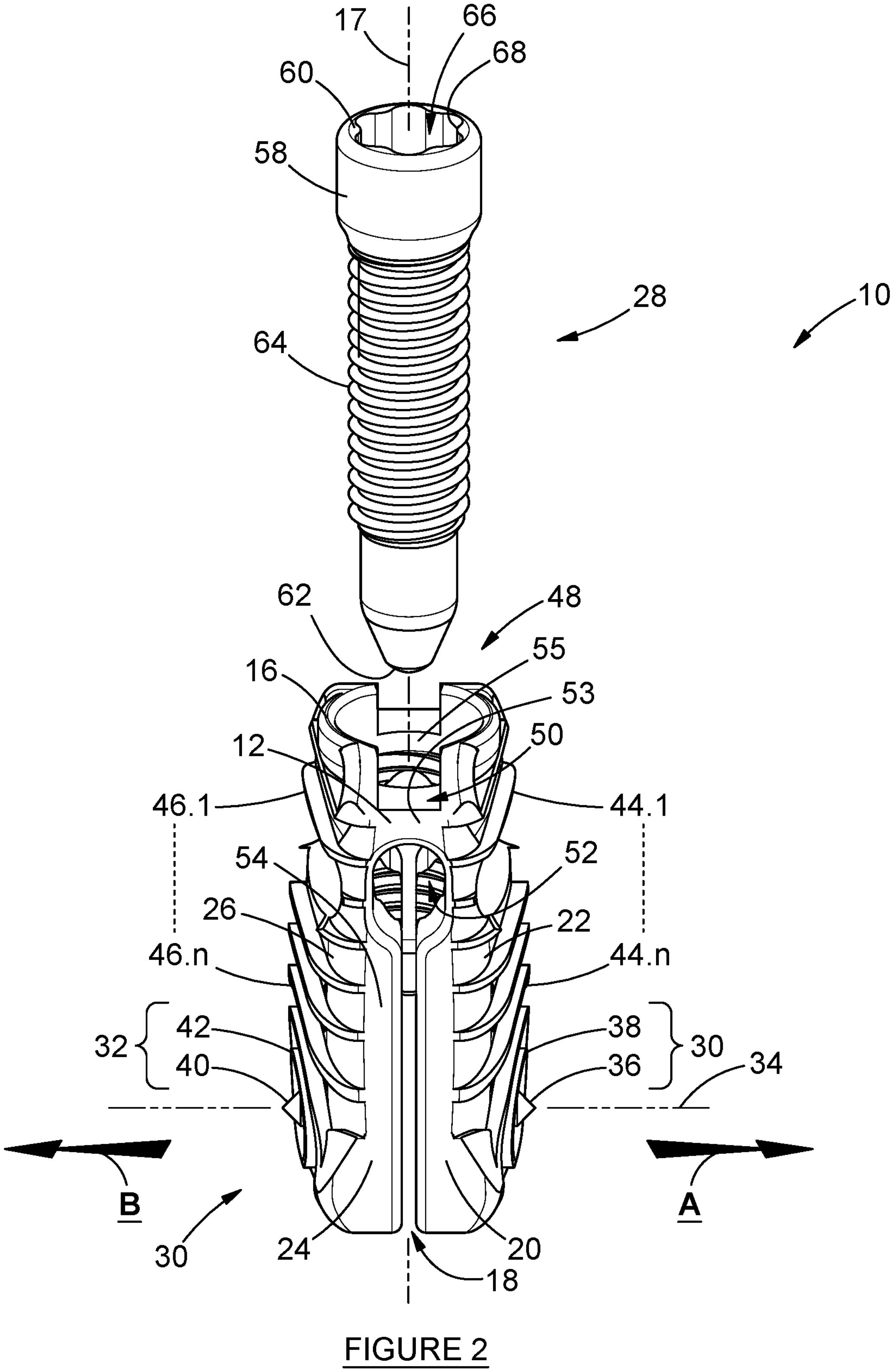
FIG. 2 is a first side perspective view of the TLIF implant device with first and second body parts of the TLIF implant device in a first configuration.
Figure 3:
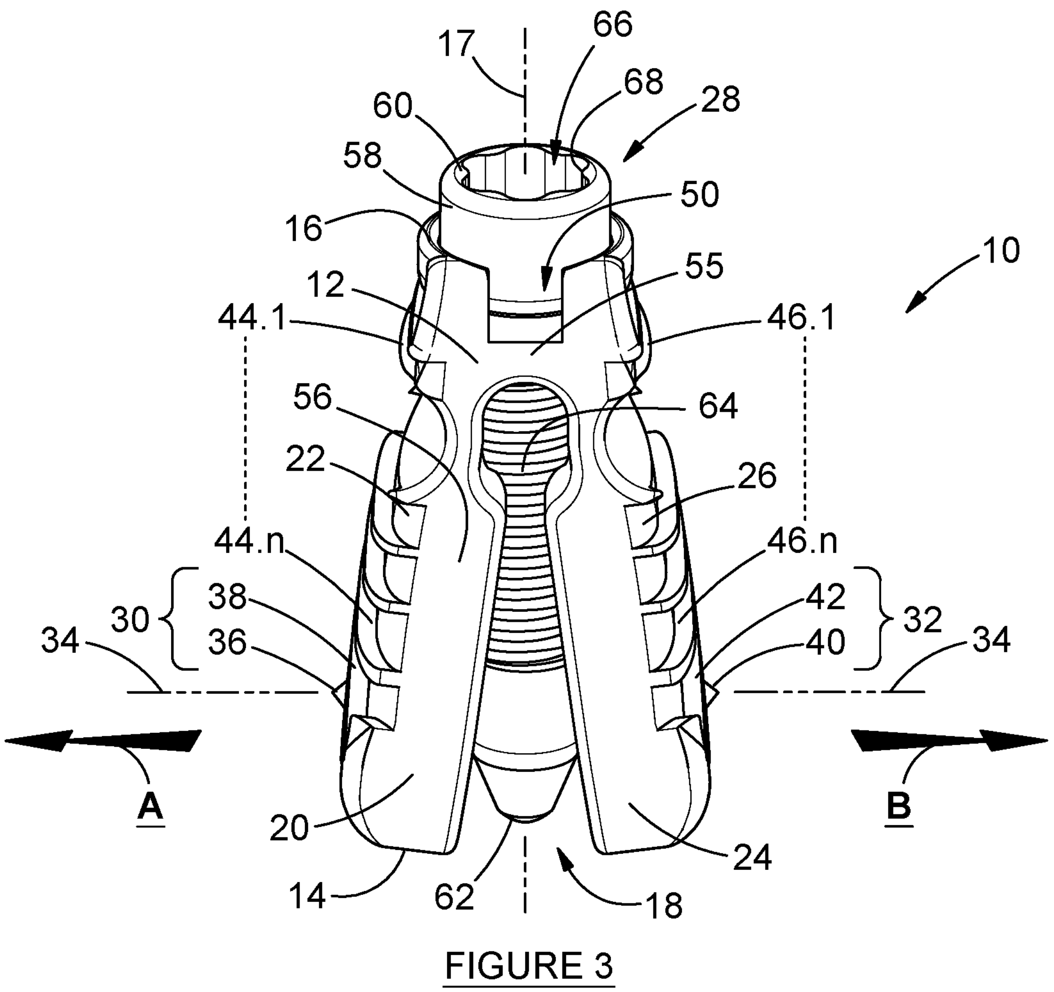
FIG. 3 is a second opposed side perspective view of the TLIF implant device with the first and second body parts of the TLIF device in a second configuration.

Referring to FIGS. 1 to 3, the TLIF device 10 comprises an elongate implant body 12 having opposed first and second ends 14, 16. The implant body 12 has a longitudinal axis 17. The implant body 12 defines a slot 18 between the first and second ends 14, 16. The slot 18 divides the implant body 12 into a first body part 20 having a first surface 22 and a second body part 24 having a second surface 26. In use, and when the implant body 12 is located in an intervertebral space 74 the first surface 22 faces towards a first vertebra 70 in a first direction A and the second surface 26 faces towards a second vertebra 78 in an opposite direction B. The second vertebra 78 is adjacent to the first vertebra 70. The first vertebra 70, the intervertebral space 74 and the second vertebra 78 are described further below and with reference to FIGS. 6 to 9. The TLIF device 10 comprises an actuator 28, a first pivot formation 30 and a second pivot formation 32.

The first and second pivot formations 30, 32 are located on an axis 34 of the implant body 12, on the first and second surfaces 22, 24 respectively and towards the first end 14. The first and second pivot formations 20, 32 are integrally formed with the body 12. The axis 34 is transverse to the longitudinal axis 17. Preferably, the transverse axis 34 is perpendicular to the longitudinal axis 17. In the embodiment shown, the first pivot formation 30 comprises a first pin 36 and at least a first circular formation 38. The second pivot formation 32 comprises a second pin 40 and at least a second circular formation 42. In the embodiment shown, the first and second pins 36, 40 are conical in shape. In alternative embodiments, not shown the first and second pins may be shaped to be any one of cylindrical and half-spherical. Each of the first and second circular formations 38, 42 has a centre point which is located on the transverse axis 34.

The implant body 12 comprises a plurality of arc formations 44.1 to **44.*n*, 46.1 to 46.*n* located on the first and second surfaces 22, 26 respectively. Each of the arc formations 44.1 to 44.*n*, 46.1 to 46.*n* has a centre point which is located on the transverse axis 34**.

As best shown in FIG. 2, the implant body 12 defines an opening 48 and a notch 50 at the second end 16. The implant body 12 comprises an internal thread 52 adjacent the opening 48.

Figure 4:
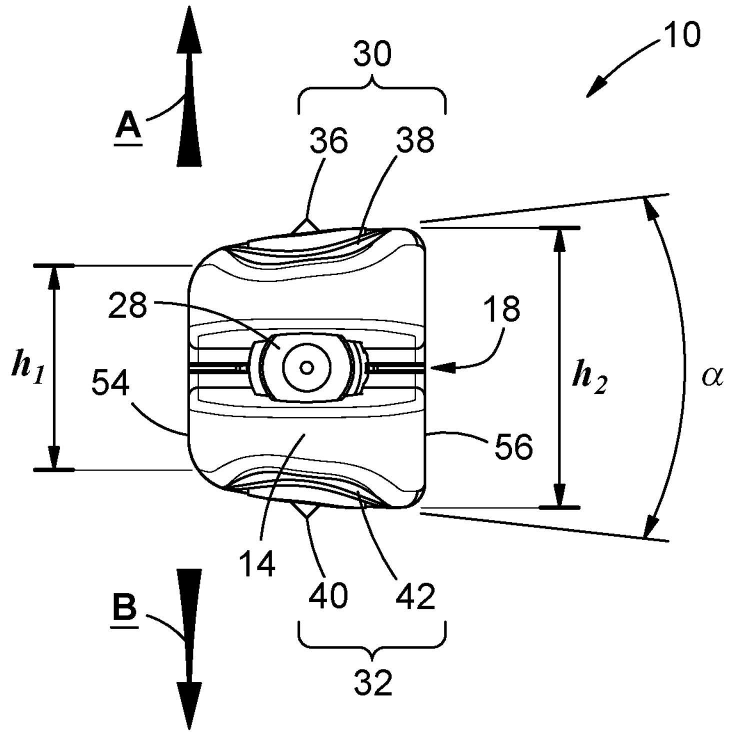
FIG. 4 is a front view of the TLIF implant device and with the first and second body parts in the first configuration.
Figure 5:
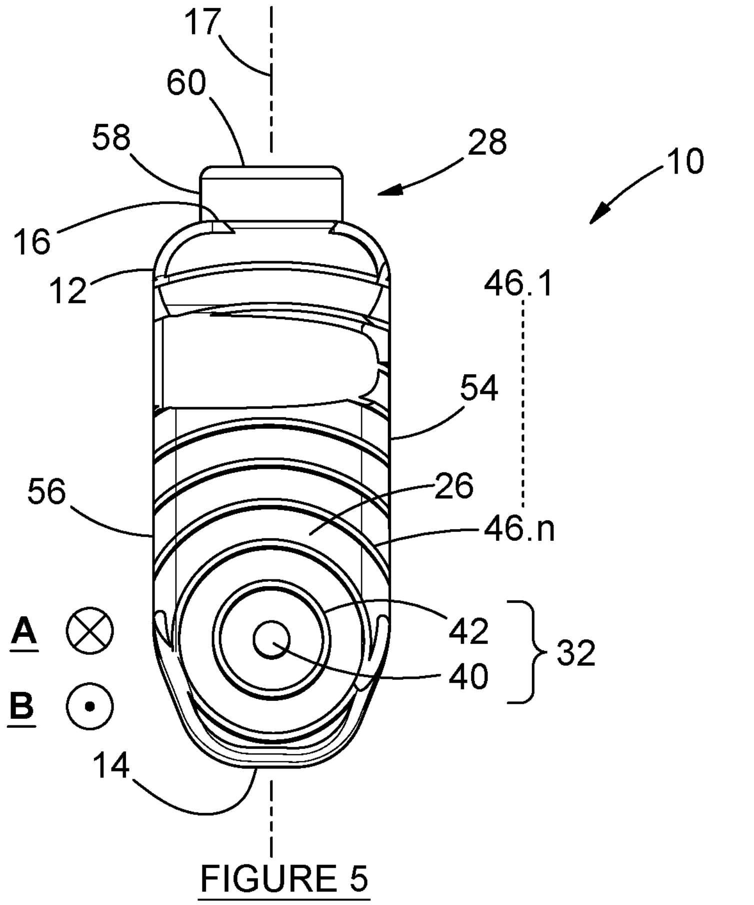
FIG. 5 is a plan view of the TLIF implant device.

The implant body 12 comprises first and second links 53, 55 between the first and second body parts 20,24. The first and second links 53, 55 are located toward the second end 14. The first and second links 53, 55 are integrally formed with the body 12. The links are preferably made of a resiliently deformable material, such as titanium. As best shown in FIG. 4, the implant body 12 has a first side 54 and a second side 56. Both the first and second sides 54, 56 are located between the first end 14 and the second end 16 and between the first surface 22 and the second surface 26. The first side 54 has a first height $h_1$ and the second side 56 has a second height $h_2$ which is more than the first height $h_1$. The first body part 20 and the second body part 24 are tapered from the second side 56 towards the first side 54 such that an angle $\alpha$ is formed between the first surface 22 and the second surface 26. In the embodiment shown the angle $\alpha$ is 11°. In alternative embodiments, the angle $\alpha$ ranges from 1° to 20°.

In yet further alternative embodiments, not shown, the second height $h_2$ may be the same as or less than the first height $h_1$. In such alternative embodiments, the first and second surfaces 22, 26 may be sloped from the first and second sides 54 towards the pivot formations 30, 32.

As best shown in FIGS. 2 and 3, the actuator 28 comprises a bolt 58 having first end 60 and a second end 62. The actuator 28 comprises an external thread 64 between the first end 60 and the second end 62. The actuator 28 defines a socket 66 extending from the first end 60 towards the second end 62. The actuator 28 comprises abutment formations 68 adjacent the socket 66 and towards the first end 60. The actuator 28 comprises an internal thread (not shown) adjacent the socket 66 and towards the second end 62.

Also as best shown in FIGS. 2 and 3, both the first surface 22 and second surface 26 are curved between the first end 14 and the second end 16 respectively.

In the embodiment shown the implant body 12 is of unitary construction. In alternative embodiments, not shown, the implant body 12 may be non-unitary and may comprise separate body parts.

The implant body 12 is preferably made of a resiliently deformable material, such as titanium.

Referring to FIGS. 1 and 2, the implant body 12 is configured such that the first and second body parts 20, 24 are biased towards a first configuration wherein the first and second surfaces 22, 26 are relatively closer to each other. The resilient deformability of the links 53, 55 causes the first and second body parts to be biased towards the first configuration.

Referring to FIGS. 3 and 4, the slot 18 is configured to receive the actuator 28 and the internal thread 52 is configured to cooperate with the external thread 64. When the actuator 28 is manipulated by a surgeon (not shown), the internal thread 52 cooperates with the external thread 64 and causes the actuator 28 to be received by the slot 18. The actuator 28 urges the first and second body parts 20, 24 to a second configuration wherein the first and second surfaces 22, 26 are relatively further away from each other.

Figure 6:
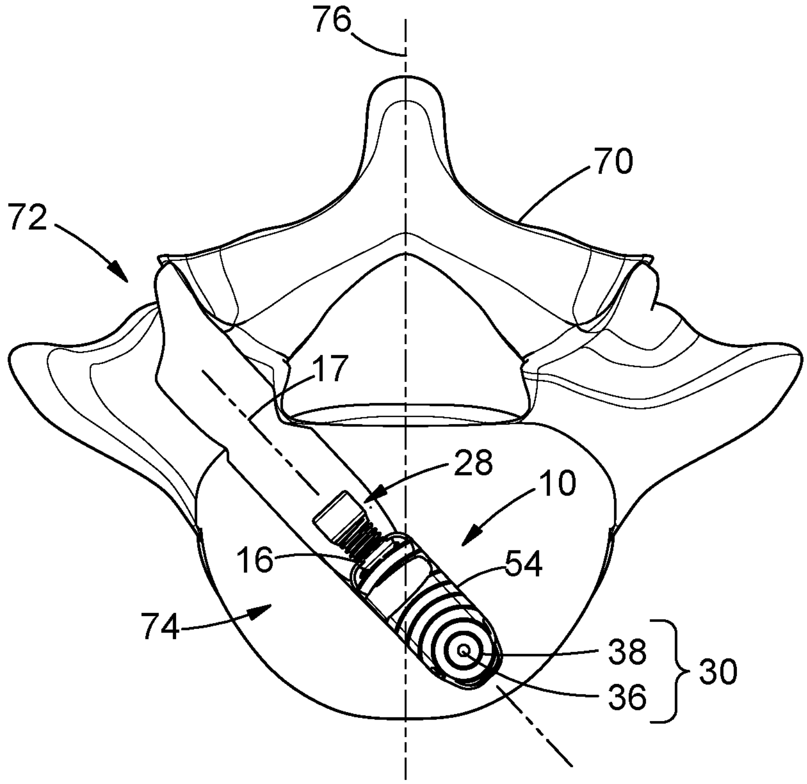
FIG. 6 is a superior view of a vertebra and shows a first TLIF implant device in use (located in an initial position) and relative to the vertebra.

Referring to FIG. 6, a first TLIF device 10 is implanted by the surgeon (not shown) as follows. The surgeon makes an incision through skin and soft tissue of a patient (not shown) to expose a posterior region of the first vertebra 70. Then, the surgeon creates a passage 72 through the first vertebra 70, to access the intervertebral space 74 (best shown in FIG. 8). The passage 72 extends from the posterior region of the first vertebra 70 and from a first side of a midline 76 of the first vertebra 70 to the intervertebral space 74. Once the passage 72 is created, the surgeon removes an intervertebral disk (not shown) from the intervertebral space 74. Then, the surgeon attaches the first TLIF device 10 to a tool 110 (described further below and shown in FIGS. 10 and 11 only), orientates the first TLIF device 10 correctly relative to the first vertebra 70, inserts the first TLIF device 10 through the passage 72 and locates first TLIF device 10 in an initial position.

In the initial position, the first side 54 faces towards the posterior region of the first vertebra 70 and the first and second pivot formations 30, 32 are located on a second opposed side of the midline 76. Whilst the first TLIF device 10 is in the initial position, the surgeon uses the tool 110 to manipulate the actuator 28, to urge the first and second body parts 20, 24 to the second configuration. Once the first and second body parts 20, 24 are in the second configuration, the surgeon detaches the tool 110 from the first TLIF device 10 and removes the tool 110 from the patient. In use, when first and second body parts 20, 24 are in the second configuration, at least the first and second pivot formations 30, 32 abut against the first vertebra 70 and second vertebra 78 (shown in FIG. 8) respectively. With the first and second pivot formations 30, 32 in abutment with the vertebrae, the first TLIF device 10 is pivotable about the transverse axis 34. When first and second body parts 20, 24 are in the second configuration, the first and second surfaces 22, 26 may also abut the first and second vertebrae 70, 74 respectively.

Figure 7:
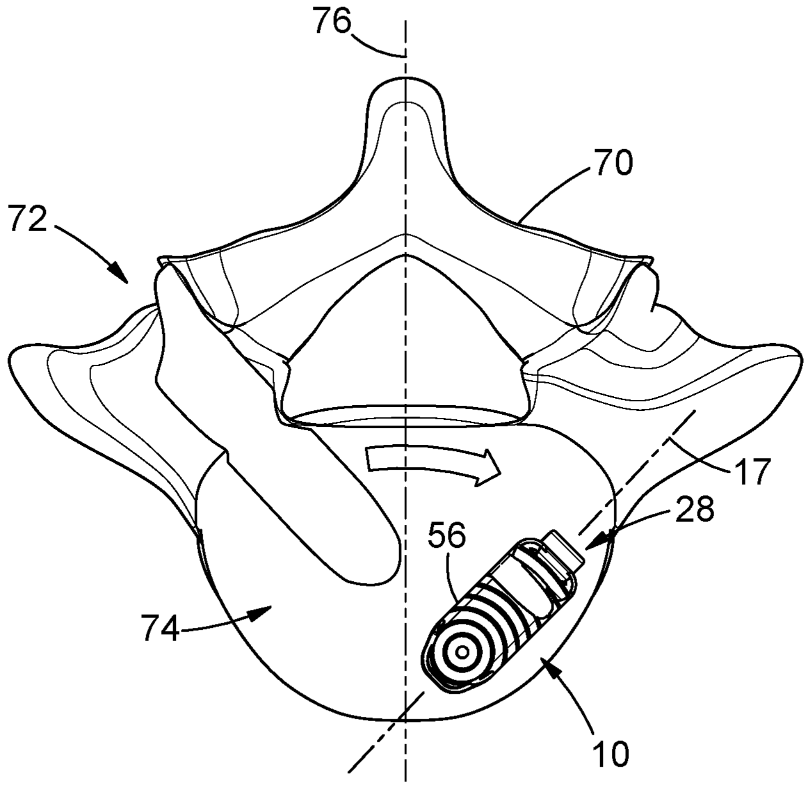
FIG. 7 is a superior view of the vertebra and shows the first TLIF implant device in use (located in a final position) and relative to the vertebra.

Referring to FIG. 7, the surgeon pivots the first TLIF device 10 from the initial position to a final position. In the final position, the second side 56 faces towards the posterior region of the first vertebra 70.

Figure 8:
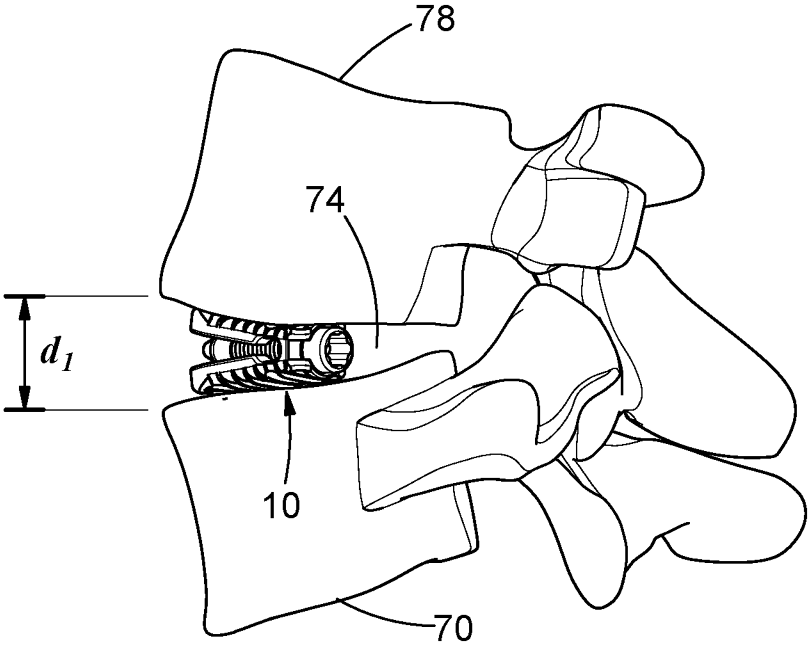
FIG. 8 is a perspective view of the first TLIF implant device with the first and second body parts in a second configuration and located in an intervertebral space.

Referring to FIG. 8, the first TLIF device 10 is in the final position and spaces the first vertebra 70 and the second vertebra 78 a pre-determined distance $d_1$ apart from each other.

Figure 9:
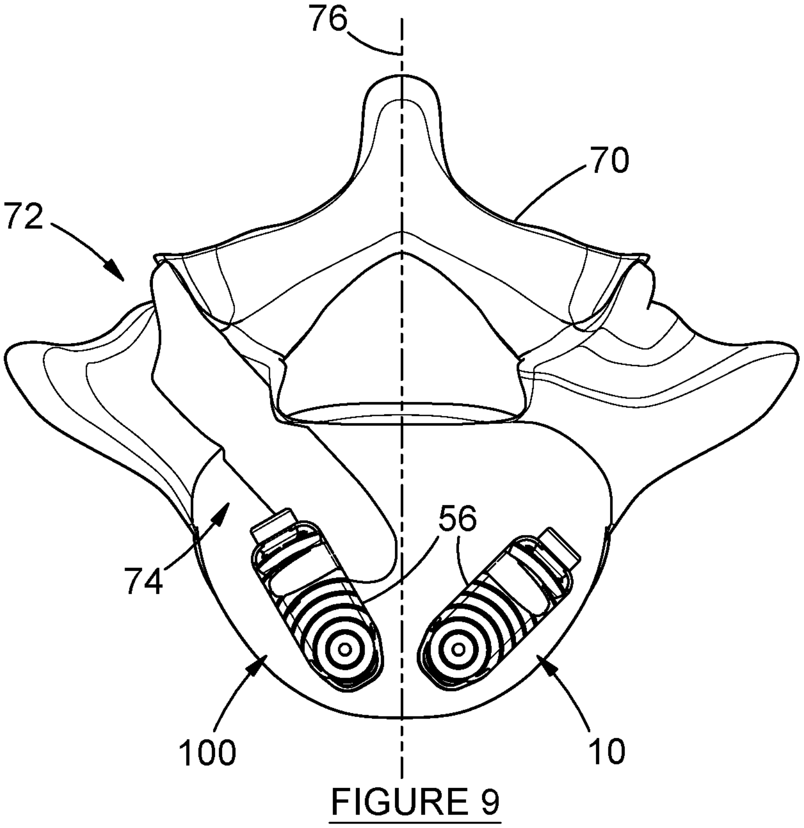
FIG. 9 is a superior view of the vertebra and shows the first TLIF implant device and a second TLIF implant device relative to the vertebra.

Referring to FIG. 9, with the first TLIF device 10 in the final position, a second TLIF device 100 can be inserted through the passage 72. The second TLIF device is similar in configuration to the first TLIF device 10 and like parts are indicated by like reference numerals. Similarly, as in the case of the first TLIF device 10, the surgeon attaches the second TLIF device 100 to the tool 110 (shown in FIGS. 10 and 11), orientates the second TLIF device 100 correctly relative to the first vertebra 70, inserts the second TLIF device 100 through the passage 72 and locates the second TLIF 100 device in a first position. In the first position, the second side 56 faces towards the posterior region of the first vertebra 70 and the first and second pivot formations 30, 32 are located on the first side of the midline 76. Then, the surgeon manipulates the actuator 28 to urge the first and second body parts 20, 24 to the second configuration. Once the first and second body parts 20, 24 are in the second configuration, the surgeon detaches the tool from the second TLIF device 100 and removes the tool 110 from the patient.

Figure 10:
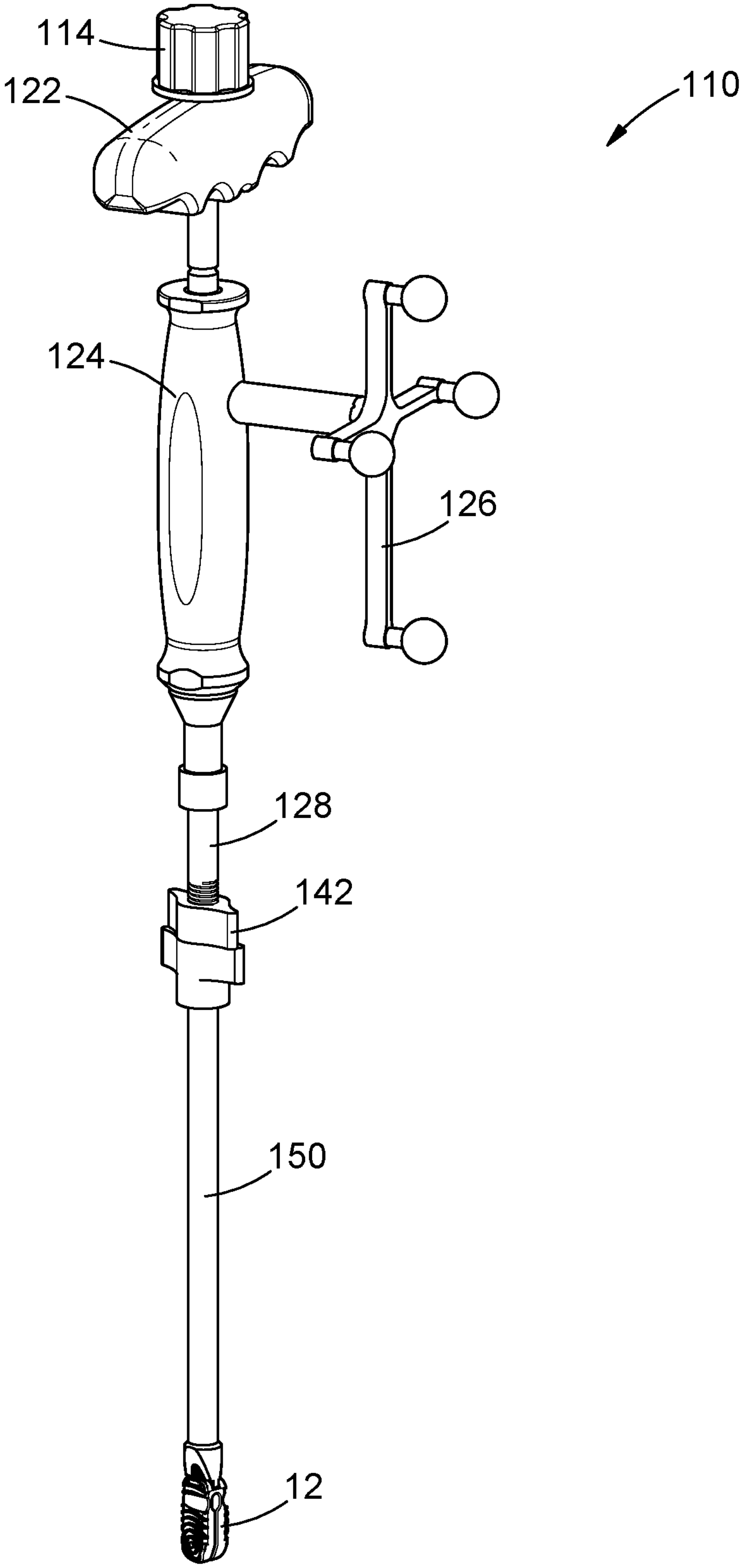
FIG. 10 is a perspective view of the TLIF implant device attached to a tool for inserting the TLIF implant device and for manipulating the actuator.
Figure 11:
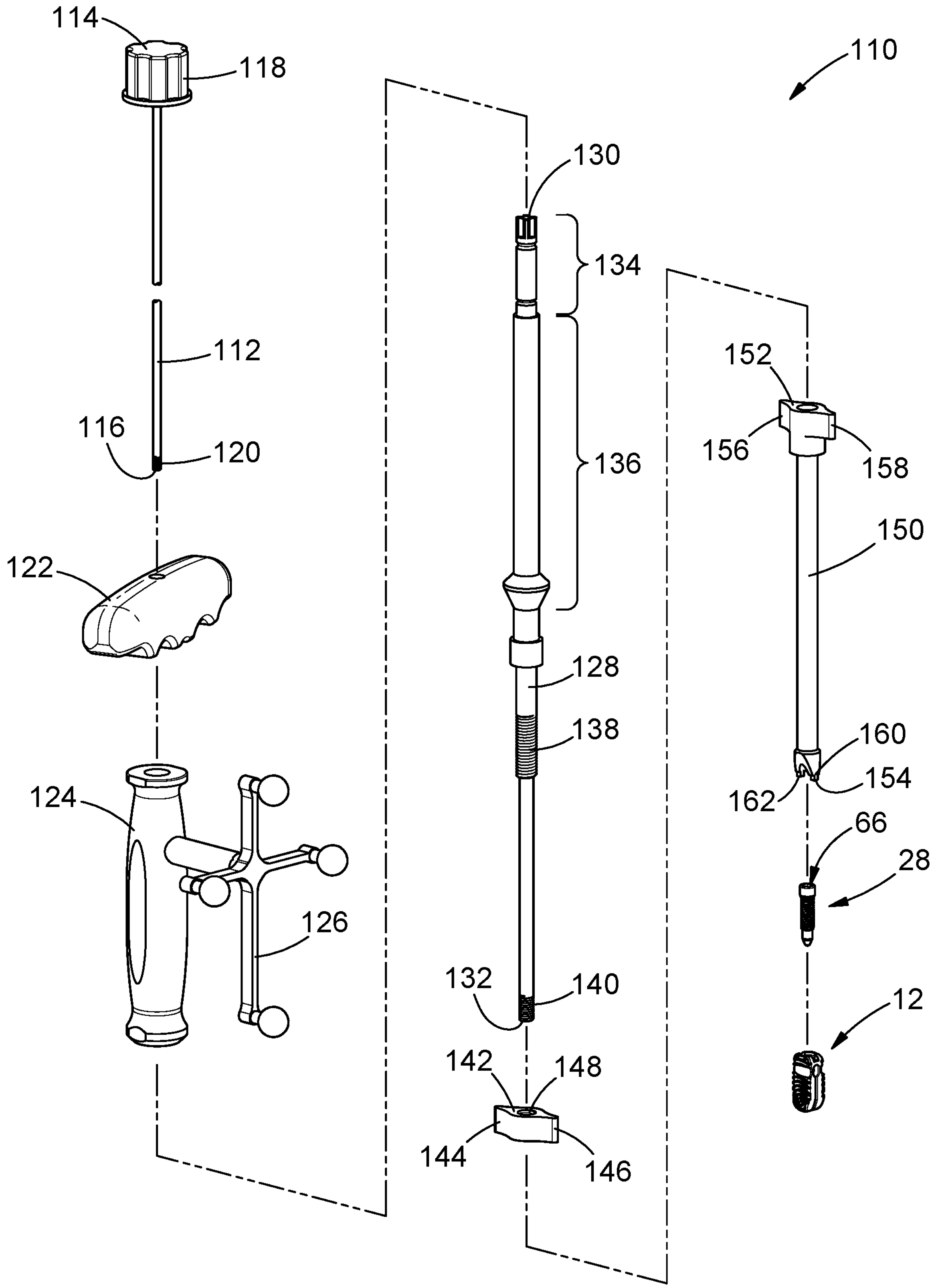
FIG. 11 is an exploded perspective view of the tool and the TLIF implant device.

FIGS. 10 and 11 shows the tool 110 (also known as an introducer) for inserting the first and second TLIF devices 10, 100 and for manipulating the actuator 28.

Referring to FIG. 11, the tool 110 comprises an elongate rod 112 having a first end 114 and an opposed second end 116. The elongate rod 112 comprises a knob 118 at the first end 114 and an external thread 120 at the second end 116.

The tool 110 comprises a handle 122 defining a socket (not shown).

The tool 110 comprises a carrier 124 of a reference array 126 of a surgical navigation system (not shown).

The tool 110 comprises an elongate shaft 128 having a first end 130 and an opposed second end 132. The elongate shaft 128 comprises a first part 134 located towards the first end 130. The elongate shaft 128 comprises an interface formation 136 located between the first part 134 and the second end 134. The elongate shaft 128 comprises an external thread 138 located between the interface formation 136 and the second end 134. The elongate shaft 128 comprises a spigot formation 140 at the second end 134. The elongate shaft 128 defines a bore (not shown) which extends from the first end 130 to the second end 134.

The tool 110 comprises a nut 142 having wing formations 144, 146. The nut 142 comprises an internal thread 148.

The tool 110 comprises an elongate tube 150 having a first end 152 and a second end 154. The elongate tube 150 comprises handle formations 156, 158 towards the first end 152. The elongate tube 150 comprises first and second prongs 160, 162 located at the second end 154.

The tool 110 is configured as follows. The interface formation 130 is configured for removably receiving the carrier 124 of the reference array 126 of a surgical navigation system (not shown). The socket (not shown) of the handle 122 is configured to receive the first part 134. The rod 112 and the shaft 128 are configured such that the rod 112 is axially receivable by the shaft 128. The shaft 128 and the nut 142 are configured such that the external thread 138 and the internal thread 148 are complementary to each other. The spigot formation 140 is configured complementary to the socket 66. The shaft 128 and the tube 150 are configured such that the shaft 128 is axially receivable by the tube 150.

In use, the tool 110 is typically assembled as follows. The carrier 124 of the reference array 126 of a surgical navigation system (not shown) is located on the interface formation 130 in socket-spigot fashion. The handle 122 is located on the first part 128, by inserting the first part 128 in the socket (not shown) of the handle 122. The rod 112 is inserted into the shaft 128 by inserting the second end 116 into the bore (not shown) from the first end 130 of the shaft 122. The rod 112 is threaded through the shaft 122 until the second end 116 extends beyond the second end 132. The nut 142 is rotated onto the external thread 138. Then, the rod 112 and shaft 122 are inserted into the tube 150 by inserting the second ends 116 and 132 at the first end 152. The rod 112 and shaft 128 are threaded through the tube 150 until the second end 116 extends beyond the second end 154.

For the TLIF device 10 to be attachable to the assembled tool 100, the actuator 28 must be at least partially received by the slot 18. This is the case when the external thread 64 is at least partially engaged with the internal thread 52.

First, the assembled tool 110 is loosely attached to the TLIF device 10 by inserting the second end 116 into the socket 66 and by engaging the external thread 120 with the internal thread (not shown) of the actuator 28. With the external thread 120 and the internal thread of the actuator 28 in engagement and by rotating the knob 118 in a first direction about a longitudinal axis (not shown) of the rod 112, the elongate body 12 is urged towards the second end 154. Correspondingly, to detach the TLIF device 10 from the tool 110, the knob 118 must be rotated in a second opposite direction about the longitudinal axis (not shown) of the rod 112.

To attach the TLIF device 10 securely to the tool 110, the knob 118 must be rotated in the first direction until a) the first and second prongs 160, 162 are seated in the notch 50 and b) the first end 152 abuts against the nut 142. The nut 142 serves to limit displacement between the tube 150 and the shaft 128. By changing a position of the nut 142 a distance between the first end 124 and the second end 150 can be changed. As such, the nut 142 can be positioned such that the distance between the first end 124 and the second end 150 is a predetermined distance.

This allows the tool 110 and TLIF device 10 to be used in combination with the surgical navigation system (not shown). In particular, this allows the surgical navigation system (not shown) to present real-time virtual images of the position and orientation of the tool 110 and TLIF implant device 10 relative to the first and second vertebrae 70, 78 of the patient.

The tool 110 and TLIF device 10 are configured such that when the TLIF device 10 is securely attached to the tool 110, the spigot formation 140 is received within the socket 66. Therefore, when the TLIF device 10 is securely attached to the tool 110, the tool 110 can be used to manipulate the actuator 28 as follows. First, the nut 142 is displaced slightly away from the first end 152. This is done by using the wing-like formations 144, 146 to rotate the nut 142 in an anti-clockwise direction (from a user of the tool's perspective). Then, by axially rotating the shaft 128 relative to the tube 150 the actuator 28 is manipulated. Typically, when the shaft 128 is axially rotated in a clock-wise direction (from the user of the tool's perspective) relative to the tube 150, the actuator 28 is manipulated to urge the first and second body parts 20, 24 from the first configuration to the second configuration. Correspondingly, when the shaft 128 is axially rotated in an anti-clockwise direction, the first and second body parts 20, 24 will return to the first configuration.

A first advantage of the invention is that the TLIF implant device 10 can be inserted through the passage 72 on the first side of the midline 74 and pivoted to a final position on an opposite side of the midline 76. Thereafter, the second TLIF device 100 can be inserted through the same passage 72. This allows for less tissue invasion of the patient than with prior art implant devices, such as TLIF implant devices without pivot formations. This is because the TLIF implant devices 10, 100 require only the single passage 72 from a posterior region of the spine towards the intervertebral space 74, to be inserted in the intervertebral space 74. A person skilled in the art would appreciate that less tissue invasion results in faster patient recovery time.

Another advantage of the invention is that it may lead to shorter surgery times resulting in more time-effective and cost-effective lumbar spinal surgeries.

It will be appreciated that there are many variations in detail available on the transforaminal lumbar interbody fusion implant device as herein defined and described, without departing from the scope and spirit of the appended claims. For example, the actuator may be received in the slot from the first end of the elongate body.

The invention claimed is:

1. A transforaminal lumbar interbody fusion implant device comprising:
- an elongate implant body having opposed first and second ends, the implant body having a longitudinal axis and the implant body defining a slot between the first end and second end dividing the implant body into:
  - a first body part having a first surface which in use, and when the body is located in an intervertebral space, faces in a first direction towards a first vertebra; and
  - a second body part having a second surface which in use, and when the body is located in the intervertebral space, faces in an opposite direction and towards a second vertebra which is adjacent to the first vertebra,
- the first and second body parts being biased towards a first configuration wherein the first and second surfaces are relatively closer to each other, the slot being configured to receive an actuator for urging the first and second body parts to a second configuration wherein the first and second surfaces are relatively further away from each other; and
- first and second pivot formations located towards the first end, and on an axis transverse to the longitudinal axis of the implant body and on the first and second surfaces respectively for enabling pivotal movement of the implant body about the transverse axis.

2. The transforaminal lumbar interbody fusion implant device as claimed in claim 1 wherein the transverse axis is perpendicular to the longitudinal axis.

3. The transforaminal lumbar interbody fusion implant device as claimed in claim 1 wherein the implant body is of unitary construction.

4. The transforaminal lumbar interbody fusion implant device as claimed in claim 1 wherein the implant body is manufactured of a resiliently deformable material.

5. The transforaminal lumbar interbody fusion implant device as claimed in claim 1 wherein the device comprises an actuator which is selectively manipulatable to urge the first and second body parts to the second configuration.

6. The transforaminal lumbar interbody fusion implant device as claimed in claim 1 wherein the slot extends from the first end towards the second end.

7. The transforaminal lumbar interbody fusion implant device as claimed in claim 1 wherein the implant body comprises at least one link between the first body part and the second body part.

8. The transforaminal lumbar interbody fusion implant device as claimed in claim 7 wherein the at least one link is integrally formed with the body.

9. The transforaminal lumbar interbody fusion implant device as claimed in claim 7 wherein the at least one link is resiliently deformable.

10. The transforaminal lumbar interbody fusion implant device as claimed in claim 1 wherein the implant body defines an opening at the second end for receiving the actuator.

11. The transforaminal lumbar interbody fusion implant device as claimed in claim 10 wherein the actuator comprises a bolt having an external thread and the implant body comprises an internal thread located adjacent the opening for cooperating with the external thread.

12. The transforaminal lumbar interbody fusion implant device as claimed in claim 1 wherein the first and second pivot formations comprise at least one of: pins and circular formations.

13. The transforaminal lumbar interbody fusion implant device as claimed in claim 1 wherein the implant body has first and second opposed sides, each side located between the first and second ends and between the first and second surfaces, and the first and second surfaces are sloped from the first side having a first height ($h_1$) towards the second side having a second height ($h_2$) which is more than the first height.

14. The transforaminal lumbar interbody fusion implant device as claimed in claim 13 wherein the first and second body parts are tapered from the second side towards the first side such that an angle ($\alpha$) is formed between the first and second surface.

15. The transforaminal lumbar interbody fusion implant device as claimed in claim 14 wherein the angle ($\alpha$) is 11°.

16. A kit comprising:

at least one transforaminal lumbar interbody fusion implant device as claimed in claim 1; and a tool for inserting the at least one device between adjacent vertebrae and for manipulating the actuator.

17. A method of implanting a transforaminal lumbar interbody fusion implant device, the device comprising a) an elongate implant body having opposed first and second ends and a longitudinal axis, the body comprising a first body part and a second body part; b) first and second pivot formations located towards the first end, on the first and second body parts respectively, and on an axis transverse to the longitudinal axis of the implant body; and c) an actuator for urging the first and second body parts away from each other, the method comprising:

creating a first posterior passage extending from a position on a first side of a midline of a vertebra to an intervertebral space;

inserting the transforaminal lumbar interbody fusion implant device through the first passage;

locating the transforaminal lumbar interbody fusion implant device in an initial position in the intervertebral space with the first and second pivot formations on an opposed side of the midline;

manipulating the actuator to urge the first and second body parts away from each other; and pivoting the transforaminal lumbar interbody fusion implant device about the transverse axis to a final position in which the second end is located on the opposed side of the midline.

18. The method as claimed in claim 17, the method further comprising:

inserting a second transforaminal lumbar interbody fusion implant device through the first passage; and locating the second transforaminal lumbar interbody fusion implant device in a position in the intervertebral space on the first side of the midline.

* * * * *